(12) United States Patent
Lee

(10) Patent No.: US 9,247,932 B2
(45) Date of Patent: Feb. 2, 2016

(54) RETRACTION SYSTEM FOR LAPAROSCOPIC SURGERY

(76) Inventor: Jeong Sam Lee, Gwangju (KR)

( * ) Notice: Subject to any disclaimer, the term of this patent is extended or adjusted under 35 U.S.C. 154(b) by 269 days.

(21) Appl. No.: 13/878,015

(22) PCT Filed: Jul. 26, 2011

(86) PCT No.: PCT/KR2011/005497
§ 371 (c)(1),
(2), (4) Date: Apr. 5, 2013

(87) PCT Pub. No.: WO2012/111891
PCT Pub. Date: Aug. 23, 2012

(65) Prior Publication Data
US 2013/0190572 A1    Jul. 25, 2013

(30) Foreign Application Priority Data
Feb. 18, 2011 (KR) .......................... 10-2011-0014308

(51) Int. Cl.
*A61B 1/32* (2006.01)
*A61B 17/02* (2006.01)
*A61B 17/122* (2006.01)
(Continued)

(52) U.S. Cl.
CPC ......... *A61B 17/0281* (2013.01); *A61B 17/0218* (2013.01); *A61B 17/122* (2013.01); *A61B 17/1227* (2013.01); *A61B 17/1285* (2013.01); *A61B 2017/00265* (2013.01); *A61B 2017/00283* (2013.01); *A61B 2017/00287* (2013.01);
(Continued)

(58) Field of Classification Search
CPC ..................... A61B 2017/0225; A61F 2/0045; A61F 2/0063; A61F 2002/0072
USPC ............ 600/37, 201, 204–209; 606/151, 185
See application file for complete search history.

(56) References Cited

U.S. PATENT DOCUMENTS 5,183,465 A    2/1993 Xanthakos et al.
5,242,456 A *  9/1993 Nash et al. .................... 606/142
(Continued)

FOREIGN PATENT DOCUMENTS

EP    2 283 778     2/2011
JP    10-118074     5/1998
(Continued)

OTHER PUBLICATIONS

International Search Report for PCT/KR2011/005497 mailed Mar. 14, 2012.

*Primary Examiner* — Eduardo C Robert
*Assistant Examiner* — Michelle C Eckman
(74) *Attorney, Agent, or Firm* — Revolution IP, PLLC

(57) ABSTRACT

The present invention relates to a retraction system for laparoscopic surgery. According to one embodiment of the present invention, the retraction system includes: a retraction part for holding an object or tissue to be retracted; a retraction fiber control part for retracting the retraction part at the area to be retracted by means of a retraction fiber to fix the retraction part; and an abdominal wall fixer coupled to the retraction fiber control part, wherein the abdominal wall fixer is fixed to the abdominal wall. The retraction fiber control part includes: a retraction fiber control part body having a retraction hole through which the retraction fiber connected to the retraction part passes in the lower portion thereof; and a retraction fiber fixing part disposed outside the retraction fiber control part body so as to retract the retraction fiber or fix the retraction fiber such that the retraction fiber is immovable.

23 Claims, 6 Drawing Sheets

(51) Int. Cl.
*A61B 17/128* (2006.01)
*A61B 17/00* (2006.01)
*A61B 17/04* (2006.01)

(52) U.S. Cl.
CPC .............. *A61B2017/00876* (2013.01); *A61B 2017/0496* (2013.01)

(56) References Cited

U.S. PATENT DOCUMENTS

| | | | | |
|---|---|---|---|---|
| 5,337,736 | A * | 8/1994 | Reddy | 600/217 |
| 5,353,786 | A * | 10/1994 | Wilk | 600/249 |
| 5,415,666 | A * | 5/1995 | Gourlay et al. | 606/142 |
| 5,582,577 | A * | 12/1996 | Lund et al. | 600/204 |
| 6,371,968 | B1 * | 4/2002 | Kogasaka et al. | 606/190 |
| 6,540,764 | B1 * | 4/2003 | Kieturakis et al. | 606/190 |
| 6,685,628 | B2 * | 2/2004 | Vu | 600/37 |
| 6,773,418 | B1 * | 8/2004 | Sharrow et al. | 604/176 |
| 7,219,671 | B2 * | 5/2007 | Benetti | 128/898 |
| 7,867,164 | B2 * | 1/2011 | Butler et al. | 600/208 |
| 7,955,292 | B2 * | 6/2011 | Leroy et al. | 604/13 |
| 8,114,018 | B2 * | 2/2012 | Park et al. | 600/215 |
| 8,262,568 | B2 * | 9/2012 | Albrecht et al. | 600/206 |
| 8,403,837 | B2 * | 3/2013 | Okoniewski | 600/201 |
| 8,827,891 | B2 * | 9/2014 | Roberts | 600/37 |
| 8,858,538 | B2 * | 10/2014 | Belson et al. | 606/1 |
| 2002/0058959 | A1 * | 5/2002 | Gellman | 606/185 |
| 2002/0069884 | A1 * | 6/2002 | Boyd et al. | 128/898 |
| 2002/0147382 | A1 * | 10/2002 | Neisz et al. | 600/29 |
| 2002/0188169 | A1 * | 12/2002 | Kammerer et al. | 600/30 |
| 2003/0028201 | A1 | 2/2003 | Navarro et al. | |
| 2003/0135093 | A1 * | 7/2003 | Yang et al. | 600/204 |
| 2004/0050395 | A1 * | 3/2004 | Ueda et al. | 128/899 |
| 2004/0111100 | A1 * | 6/2004 | Benderev et al. | 606/151 |
| 2004/0158261 | A1 * | 8/2004 | Vu | 606/113 |
| 2005/0065409 | A1 * | 3/2005 | de la Torre et al. | 600/204 |
| 2005/0131345 | A1 * | 6/2005 | Miller | 604/117 |
| 2005/0203344 | A1 * | 9/2005 | Orban et al. | 600/204 |
| 2005/0203549 | A1 * | 9/2005 | Realyvasquez | 606/142 |
| 2006/0079921 | A1 * | 4/2006 | Nezhat et al. | 606/185 |
| 2006/0089609 | A1 * | 4/2006 | Bleich et al. | 604/272 |
| 2006/0149135 | A1 * | 7/2006 | Paz | 600/201 |
| 2006/0211919 | A1 * | 9/2006 | Wilk | 600/207 |
| 2006/0217597 | A1 * | 9/2006 | Vayser et al. | 600/249 |
| 2007/0005087 | A1 * | 1/2007 | Smith et al. | 606/185 |
| 2007/0038017 | A1 * | 2/2007 | Chu | 600/37 |
| 2007/0123852 | A1 * | 5/2007 | Deem et al. | 606/45 |
| 2007/0270890 | A1 * | 11/2007 | Miller | 606/151 |
| 2008/0021263 | A1 * | 1/2008 | Escude et al. | 600/29 |
| 2008/0027273 | A1 * | 1/2008 | Gutterman | 600/37 |
| 2008/0058603 | A1 * | 3/2008 | Edelstein et al. | 600/201 |
| 2008/0058851 | A1 * | 3/2008 | Edelstein et al. | 606/185 |
| 2008/0091215 | A1 * | 4/2008 | Saleh | 606/113 |
| 2008/0262527 | A1 * | 10/2008 | Eder et al. | 606/185 |
| 2008/0281344 | A1 * | 11/2008 | Morisseau | 606/185 |
| 2008/0294184 | A1 * | 11/2008 | Smith | 606/185 |
| 2008/0300545 | A1 * | 12/2008 | Hsieh | 604/167.03 |
| 2009/0005800 | A1 * | 1/2009 | Franer et al. | 606/185 |
| 2009/0062618 | A1 * | 3/2009 | Drew et al. | 600/204 |
| 2009/0093833 | A1 * | 4/2009 | Smith | 606/185 |
| 2009/0137984 | A1 * | 5/2009 | Minnelli | 604/540 |
| 2009/0149700 | A1 * | 6/2009 | Garcia et al. | 600/37 |
| 2009/0287060 | A1 * | 11/2009 | Pell et al. | 600/201 |
| 2009/0326573 | A1 * | 12/2009 | Miller | 606/193 |
| 2010/0069930 | A1 * | 3/2010 | Roslin et al. | 606/151 |
| 2010/0081864 | A1 * | 4/2010 | Hess et al. | 600/37 |
| 2010/0081883 | A1 * | 4/2010 | Murray et al. | 600/204 |
| 2010/0094094 | A1 * | 4/2010 | DeSantis et al. | 600/217 |
| 2010/0113883 | A1 * | 5/2010 | Widenhouse et al. | 600/208 |
| 2010/0130824 | A1 * | 5/2010 | Piskun | 600/204 |
| 2010/0256523 | A1 * | 10/2010 | Uznanski et al. | 600/565 |
| 2010/0292540 | A1 * | 11/2010 | Hess et al. | 600/206 |
| 2010/0292724 | A1 * | 11/2010 | Ravikumar et al. | 606/185 |
| 2010/0312051 | A1 * | 12/2010 | Brown | 600/37 |
| 2011/0054249 | A1 * | 3/2011 | Narthasilpa et al. | 600/37 |
| 2011/0054261 | A1 * | 3/2011 | Battles | 600/210 |
| 2011/0082343 | A1 * | 4/2011 | Okoniewski | 600/208 |
| 2011/0105836 | A1 * | 5/2011 | Miller | 600/37 |
| 2011/0105848 | A1 * | 5/2011 | Sadovsky et al. | 600/204 |
| 2011/0137129 | A1 * | 6/2011 | Heinrich et al. | 600/206 |
| 2011/0144442 | A1 * | 6/2011 | Farrell et al. | 600/206 |
| 2011/0144448 | A1 * | 6/2011 | Shelton et al. | 600/216 |
| 2011/0152914 | A1 * | 6/2011 | Ostrovsky et al. | 606/193 |
| 2011/0319988 | A1 * | 12/2011 | Schankereli et al. | 623/2.11 |
| 2012/0016203 | A1 * | 1/2012 | King | 600/204 |
| 2012/0078057 | A1 * | 3/2012 | Scott | 600/201 |
| 2012/0179001 | A1 * | 7/2012 | Taylor et al. | 600/208 |
| 2012/0232334 | A1 * | 9/2012 | Bell et al. | 600/37 |
| 2012/0238824 | A1 * | 9/2012 | Widenhouse et al. | 600/207 |
| 2012/0238825 | A1 * | 9/2012 | Smith | 600/207 |
| 2012/0316593 | A1 * | 12/2012 | Kim | 606/185 |
| 2013/0012765 | A1 * | 1/2013 | Vemuri et al. | 600/30 |
| 2013/0035555 | A1 * | 2/2013 | Alexander et al. | 600/207 |
| 2013/0060094 | A1 * | 3/2013 | Lee | 600/207 |
| 2013/0066145 | A1 * | 3/2013 | Fairneny et al. | 600/37 |
| 2013/0103057 | A1 * | 4/2013 | Keating et al. | 606/146 |
| 2013/0109910 | A1 * | 5/2013 | Alexander et al. | 600/37 |
| 2013/0109924 | A1 * | 5/2013 | Gan | 600/205 |
| 2013/0110156 | A1 * | 5/2013 | Nakayama et al. | 606/205 |
| 2013/0172682 | A1 * | 7/2013 | Ransden et al. | 600/204 |
| 2013/0172684 | A1 * | 7/2013 | Smith | 600/208 |
| 2013/0178711 | A1 * | 7/2013 | Avneri et al. | 600/208 |
| 2013/0178885 | A1 * | 7/2013 | Lee | 606/185 |
| 2013/0184255 | A1 * | 7/2013 | Shibley et al. | 600/235 |
| 2013/0190572 | A1 * | 7/2013 | Lee | 600/204 |
| 2013/0190573 | A1 * | 7/2013 | Smith | 600/207 |
| 2013/0217954 | A1 * | 8/2013 | Danna et al. | 600/30 |
| 2013/0225936 | A1 * | 8/2013 | Alexander et al. | 600/235 |
| 2013/0237768 | A1 * | 9/2013 | Heftman | 600/228 |
| 2013/0253275 | A1 * | 9/2013 | Ransden et al. | 600/204 |
| 2013/0253279 | A1 * | 9/2013 | Smith | 600/204 |
| 2013/0261651 | A1 * | 10/2013 | Zhou | 606/185 |
| 2013/0267981 | A1 * | 10/2013 | Zhou | 606/185 |
| 2013/0274759 | A1 * | 10/2013 | Oskin et al. | 606/119 |
| 2013/0281787 | A1 * | 10/2013 | Avneri et al. | 600/208 |
| 2013/0317308 | A1 * | 11/2013 | Bonutti | 600/207 |
| 2013/0338706 | A1 * | 12/2013 | Jimenez et al. | 606/213 |
| 2014/0031630 | A1 * | 1/2014 | Nguyen | 600/204 |
| 2014/0066717 | A1 * | 3/2014 | Rogers et al. | 600/201 |
| 2014/0121464 | A1 * | 5/2014 | Lonky | 600/204 |
| 2014/0172000 | A1 * | 6/2014 | Kuntz et al. | 606/185 |
| 2014/0179991 | A1 * | 6/2014 | Miller | 600/37 |
| 2014/0235936 | A1 * | 8/2014 | Baas et al. | 600/37 |
| 2014/0235951 | A1 * | 8/2014 | Fischvogt | 600/208 |
| 2014/0243599 | A1 * | 8/2014 | Farin et al. | 600/114 |
| 2014/0243601 | A1 * | 8/2014 | Kleyman | 600/204 |
| 2014/0257027 | A1 * | 9/2014 | Palmisano et al. | 600/37 |
| 2014/0257031 | A1 * | 9/2014 | Gobron et al. | 600/37 |
| 2014/0257032 | A1 * | 9/2014 | Hacker et al. | 600/37 |
| 2014/0336470 | A1 * | 11/2014 | Rodriguez Fernandez et al. | 600/204 |
| 2014/0343365 | A1 * | 11/2014 | Bachar et al. | 600/204 |
| 2014/0371537 | A1 * | 12/2014 | Marczyk et al. | 600/204 |
| 2015/0025309 | A1 * | 1/2015 | Karram | 600/37 |
| 2015/0025312 | A1 * | 1/2015 | De Canniere | 600/104 |
| 2015/0032143 | A1 * | 1/2015 | Khouri | 606/186 |
| 2015/0038793 | A1 * | 2/2015 | Prior et al. | 600/204 |
| 2015/0038794 | A1 * | 2/2015 | Pattison et al. | 600/204 |
| 2015/0039025 | A1 * | 2/2015 | Prior et al. | 606/228 |
| 2015/0045624 | A1 * | 2/2015 | Stack | 600/205 |
| 2015/0073221 | A1 * | 3/2015 | Nuzziello | 600/204 |
| 2015/0073222 | A1 * | 3/2015 | Kishi | 600/204 |
| 2015/0094741 | A1 * | 4/2015 | Hodgkinson et al. | 606/145 |

FOREIGN PATENT DOCUMENTS

| | | | |
|---|---|---|---|
| JP | 2002-336264 | 11/2002 | |
| KR | 20-0449450 | 7/2010 | |
| WO | WO 2004019813 A1 * | 3/2004 | A61F 2/00 |

* cited by examiner

RETRACTION SYSTEM FOR LAPAROSCOPIC SURGERY

RELATED APPLICATIONS

This application is a 371 application of International Application No. PCT/KR2011/225497, filed Jul. 26, 2011, which in turn claims priority from Korean Patent Application No. 10-2011-0014308, filed Feb. 18, 2011, each of which is incorporated herein by reference in its entirety.

TECHNICAL FIELD

The present invention relates to a retraction system for retracting a tissue or an internal organ during surgery in terms of a surgical operation, a laparoscopic surgery, a thoracoscopic surgery or a robot-assisted operation.

BACKGROUND ART

In the field of a surgical operation, different from the typical laparoscopic surgery, the use of a laparoscopic surgery increases day by day after it was developed for the purpose of reducing an incised portion at a skin.

The laparoscopic surgery has features in that multiple small holes are formed at a patient's abdomen with trocars, and a surgical operation tool such as an endoscope, etc. is introduced up to an operation portion of an abdomen with the aid of trocars, so a doctor performs a surgical operation observing an operation portion of an abdomen through the endoscope.

The above mentioned laparoscopic surgery is widely applied to cholecystectomy, extirpation of choledocal stone, hepatolithectomy, gastrectomy, colectomy, small intestine resection, thyroidectomy, etc.

Among the surgical operation tools used for the sake of a laparoscopic surgery, the trocars has features in that one end of a trocars body integrally extends communicating with a channel with a certain size and comprises an insertion part which is inserted into a hole formed at the abdomen.

In almost surgical operation procedures, it is preferred to use as many work channels as possible which extend into a body for the purpose of allowing various tools to pass by when a certain tissue is observed for the sake of a diagnosis or treatment, and the tissue is treated holding it.

In the course of an abdomen procedure in a laparoscopic surgery, at least one tubular cannula or a retractor which forms a work channel is inserted into an abdominal cavity.

Here, a camera for a laparoscopic surgery connected to a monitor in an operation room can be used for the purpose of observing an operation portion. The above mentioned camera can be set up through one of the work channels.

Various laparoscopic surgery tools such as a grasper, a dissector, scissors, a retractor, etc. can be set up through at least one work channel for a surgical doctor and/or assistants to handle them in easier ways. In this case, an additional tool for the sake of retractions is necessary.

In addition, a view way in terms of surgical operation and a surgical operation itself might be interrupted now that a liver, uterus, intestine (small intestine (including duodenum), large intestine, rectum or stomach, etc) comes down into an operation region during the operations near a gallbladder or an esophagus or during the laparoscopic surgery in a pelvic cavity.

The laparoscopic tissue retractor of WO 09/047707 (Apr. 16, 2009) discloses a tissue reactor for a surgery which is generally used for a surgical operation. The above mentioned retractor has features in that a mesh barrier connected to a long shaft is inserted in the interior of an abdominal cavity for retracting organs.

For the above mentioned mesh barrier is connected with a long shaft and is handled through a channel, it may be interfered with other surgical tools which are used for the sake of an operation work through the channels, so some surgical tools may collide with each other because each tool works differently from others in a narrow channel.

DISCLOSURE OF INVENTION

Accordingly, it is an object of the present invention to provide a retraction system for surgical operations which makes it possible to protect other organs in an abdominal cavity and to prevent other organs from coming down into a surgical operation region by providing a means which can help lift up in safe a gallbladder, small intestine (including duodenum), large intestine, rectum and stomach during the laparoscopic surgery without damaging them.

It is another object of the present invention to provide a retraction system for surgical operations which does not cause any interruption when in operation and a view way interruption the problems of which used to happen by other organs and surgical operation tools during the surgical operations in an abdominal cavity.

It is further another object of the present invention to provide a retraction system for a laparoscopic surgery which helps reduce the number of trocars by providing a retraction system for surgical operations which can temporarily support the surgical tools which are ready for the actual uses during the surgical operations in an abdominal cavity.

It is still further another object of the present invention to provide a retraction system for a laparoscopic surgery which makes it possible to reduce the scars which are formed due to the use of surgical tools by providing an abdominal wall fixer which can be directly secured to an abdominal wall or can be secured with the aid a needle rod with a narrow diameter.

To achieve the above objects, there is provided a retraction system for a laparoscopic surgery, comprising a retraction part for holding an object or a tissue which will be retracted; a retraction fiber control part for retracting the retraction part with a retraction fiber to a retraction place and fixing the retraction part; and an abdominal wall fixer which is coupled with the retraction fiber control part and is fixed at an abdominal wall, and the retraction fiber control part comprising a retraction fiber controller body which has a retraction hole formed at its lower side for a retraction fiber connected with the retraction part to pass through the retraction hole; and a retraction fiber fixing part which is provided at an outer side of the retraction fiber control part body and retracts the retraction fiber and fixes the retraction fiber.

Here, the retraction fiber fixing part is longitudinally shaped with an acute anger with its upper side being gradually narrowed and its lower side being formed in a circular shape and comprises an insertion part which helps retract the retraction fiber through a lower side of the retraction fiber fixing part and a retraction side hole formed at the retraction fiber control part body and helps insert the retraction fiber into the acute angle portion of the upper side of the retraction fiber fixing part.

The retraction fiber fixing part comprises a pulley part which is disposed at the top of the retraction fiber control part body and guides the retraction fiber.

In addition, at an end portion of the retraction fiber passing through the retraction hole is provided a circular ring or a circular member connecting the retraction part.

In addition, the retraction part comprises a net shaped net and a tissue retractor disposed at both sides of the net and connected with the retraction fiber.

In addition, the abdominal wall fixer is a hollow cylindrical body with its upper side being open and its lower side being sealed, and the upper rim part of the cylindrical body is formed of a flexible elastic element, and the cylindrical body is made of an elastic material for the cylindrical body to inwardly transform when a laparoscopic tool grabs and to recover to its original cylindrical shape when the laparoscopic tool is released and comprises an attachable abdominal wall fixer which is attached to an inner side of the abdominal wall.

In addition, the abdominal wall fixer comprises an upper abdominal wall fixer which is secured to an outer side of the abdominal wall; and a lower abdominal wall fixer which is secured in the interior of the abdominal wall, and the upper abdominal wall fixer and the lower abdominal wall fixer are secured at the inner and outer sides of the abdominal wall with the aid of the lower abdominal wall fixer and a needle rod formed of an engaging needle hole.

The retraction system is inserted into an abdominal cavity and is separated from through a cut window provided at the abdominal wall or a trocar, and the diameter of the retraction system is 5-20 mm.

According to one aspect of the present invention, the retraction part comprises a grabber retractor, comprising a head part with a protrusion helping grab an organ or a tissue; and a grabber body part controlling an opening and closing operation of the head part, and when the grabber body part is pressed, the head part is opened, and when the pressing force is removed, the head part is closed.

The abdominal wall fixer comprise a lower abdominal wall fixed magnet part which is disposed in the interior of the abdominal wall and is formed of a magnet; and an upper abdominal wall fixed magnet part which is secured to an outer side of the abdominal wall and has a magnetism opposite to the magnetism of the lower abdominal wall fixed magnet, and the upper and lower abdominal wall fixed magnets each comprise a protection membrane surrounding the fixed magnets.

Advantageous Effects

The retraction system according to an embodiment of the present invention has advantages in that the organs such as a gallbladder, small intestine (including duodenum), large intestine, rectum and stomach can be protected during a laparoscopic surgery, and it is possible to prevent the organs from coming down into an operation region.

In the present invention, it is possible to shorten the operation time now that other organs and operation tools do not interfere with the operation proceedings and operation vie ways during the surgical operations of an abdominal cavity.

In a retraction system according to an embodiment of the present invention, the number of trocars can be reduced by providing a retraction system for surgical operations which can temporarily support operation tools which are ready for a surgical operation in an abdominal cavity for thereby reducing the scars after surgical operations.

In a retraction system for an abdominal wall support according to an embodiment of the present invention, an abdominal wall fixer which can be directly secured to an abdominal wall or can be secured with the aid a needle rod with a narrow diameter, so a scar is not formed after the use of a retraction system.

In a retraction system according to an embodiment of the present invention, the number of operation tools can be minimized in the channels of the operation trocars by providing a retraction system for surgical operations which can temporally support the operation tools which are ready for actual uses, against an abdominal wall without using an operation trocar, so it is possible to prevent any collisions between tools while retracting a certain tissue and to reduce operation time, protecting internal organs.

BEST MODES FOR CARRYING OUT THE INVENTION

Figure 1:
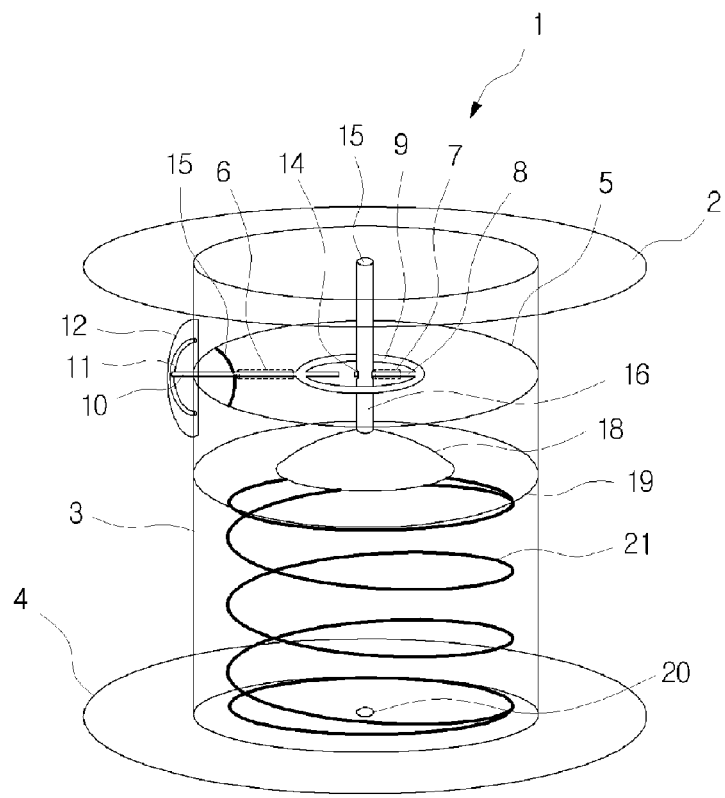
FIG. 1 is a view illustrating a construction of an upper abdominal fixer of a retraction system according to a first embodiment of the present invention.

The present invention may be modified in various forms and may have different embodiments, and specific embodiments are illustrated in the drawings and will be described in details in the detailed descriptions; however such disclosures are not intended to limit the disclosed embodiments, and all modifications and equivalents and substituent should be interpreted to belong to the concepts and technical scopes of the present inventions.

In the course of descriptions of the invention, when it is judged that the details descriptions on the related prior arts make unclear the gist of the present invention, the detailed descriptions of the invention will be omitted.

The terms such as "first", "second", etc. may be used in describing various elements; however such elements are not limited by such terms. Such terms are used only for the purpose of distinguishing a corresponding element from other elements.

The terms used in the present invention are used for the purpose of describing a specific embodiment, not intended to limit the present invention. A singular form expression means including multiple expressions unless otherwise stated. The terms "comprise" or "include" in the present invention are used to specify the presence of features, numbers, steps, operations, elements, parts or a combination of them, not intended for one or at least one feature to eliminate numbers, steps, operations, elements, parts or a combination of them.

The illustrative embodiments of the present invention will be described so as to provide a comprehensive understanding on the structure, function and use principle of the system disclosed in the present invention. At least one example of such embodiments is shown in the accompanying drawings.

The constructions specifically described in the specification and shown in the accompanying drawings are provided for the illustrative purposes, and the features which are provided in relation with the illustrative embodiments may be combined with the features of another embodiment. Such modifications and changes are intended to belong to the scope of the present invention.

The embodiments of the present invention are described in relation with the surgical operation procedures of the laparoscopic surgery in the abdominal cavity; however it should be understood that the system may be applied to all portion of a human body or an animal body or may be applied to various surgical treatment procedures. For example, the system disclosed in an embodiment of the present invention may be applied to a thoracic cage, a pelvic cavity, a cranial cavity or a certain natural hole in a human body or an artificially formed hole and may be applied to an endoscopic procedure and a robot-assisted surgical operation or an abdominal opening surgical procedure.

The embodiments of the present invention will be described in details with reference to the accompanying drawings.

The retraction system according to an embodiment of the present invention comprises a retraction part for holding an object or a tissue which will be retracted, a retraction controller for pulling the retraction part in a retraction direction and fixing the same, and an abdominal wall fixer for fixing the retraction controller at an abdominal wall.

The elements of the retraction system according to an embodiment of the present invention may be a combination of element components.

The portion that is inserted into the abdominal cavity of the retraction system according to an embodiment of the present invention has a diameter of 5-20 mm and is configured to be inserted or removed through an operation window such as a navel, etc. for a laparoscopic surgery (the diameter is generally 10 mm-20 mm) or a trocar (the diameter is generally 5 mm, 10 mm, 11 mm or 12 mm).

FIGS. 1 to 4 are views illustrating an abdominal wall fixer of a retraction system according to a first embodiment of the present invention, which serves to fix a retraction object at an abdominal wall.

Figure 2:
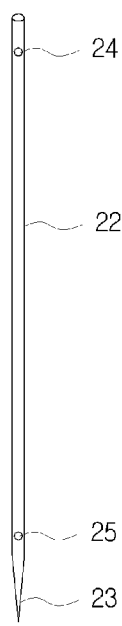
FIG. 2 is a side view illustrating a needle rod which is secured to an abdominal wall fixer according to a first embodiment of the present invention.

FIG. 1 is a view illustrating a construction of an upper abdominal fixer of a retraction system for the sake of a laparoscopic surgery according to a first embodiment of the present invention. FIG. 2 is a side view illustrating a needle rod which is secured to an abdominal wall fixer according to a first embodiment of the present invention.

The upper abdominal fixer 1 according to a first embodiment of the present invention is secured to an outer abdominal wall of an abdominal cavity.

The upper abdominal wall fixer 1 according to a first embodiment of the present invention comprises a cylindrical body 3, an upper circular plate 2 provided at the top of the cylindrical body 3, and a lower circular plate 4 which is formed below the cylindrical body 3.

At the centers of the upper circular plate 2 and the lower circular plate 4 are formed upper and lower guide holes 15 and 20 through which a needle rod secured to the abdominal wall fixer according to a first embodiment of the present invention to come in and go out.

In the upper hole 15 is provided a needle rod guide tube 16 serving to guide a needle rod toward a lower side and facilitating an easier insertion of the same, and at a lower side of the needle rod guide tube 16 is provided a hopper shaped spring guide plate support part 18 for the purpose of attaching a spring guide plate 19.

Between the spring guide plate 19 and the lower circular plate 4 is disposed a spring shaped elastic part 21.

It is preferred that the cylindrical body 3 of the upper side of the spring guide plate 19 is made of a hard material being good at maintaining a frame, and the cylindrical body 3 of the lower side of the spring guide plate 19 is made of a flexible material which can be easily folded.

At both sides of the intermediate portion of the needle rod guide tube 16 is formed an intermediate hole 14 through which a hook 8 fixing a needle rod comes in and goes out.

In other words, the hook is installed in a circular hooking part formed near the intermediate portion of the needle rod guide tube for limiting the coming-in and going-out, so the needle rod can be fixed or can be allowed to pass by.

The hook 8 is provided at an inner side of the circular hooking part 9, and a hook connection part 10 is connected to an outer portion of the other side of the circular hooking part 9.

The hook connection part 10 is connected to operate in sync with a bow shaped elastic pressing part 11 formed at the top of the cylindrical body 3.

The needle rod 22 has an upper top with a circular cross section and a sharp needle 23 formed at a lower end hard enough to pass through the abdominal wall. Needle holes 24 and 25 are formed at the upper and lower sides for the hooks 8 and 32 of the elastic pressing parts to come in and go out.

Figure 3:
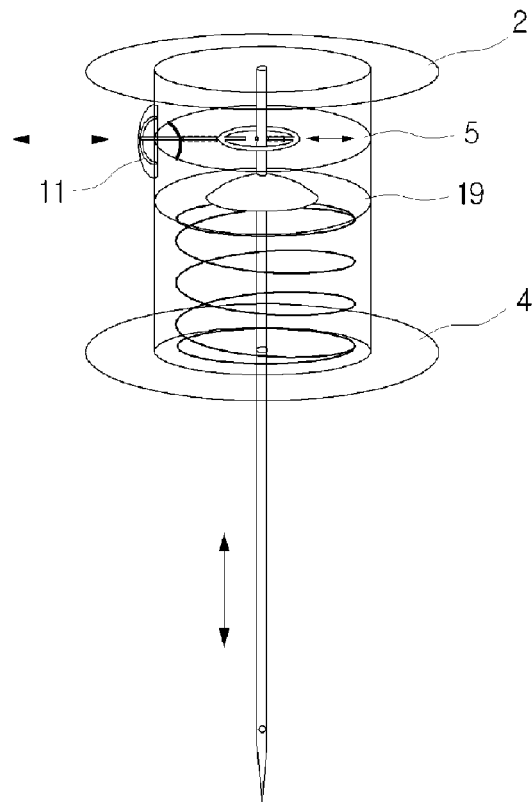
FIG. 3 is a view illustrating a construction that a needle rod is secured to an upper abdominal wall fixer according to a first embodiment of the present invention.

FIG. 3 is a view illustrating a construction that a needle rod 22 is installed at an upper abdominal wall fixer in a long and thin shape according to a first embodiment of the present invention.

The hook 8 usually remains inserted into the intermediate hole 14, and when the bow shaped elastic pressing part 11 is pressed, the hook 8 becomes disengaged from the intermediate hole 14, so the needle rod 22 becomes free in coming in and going out.

When the pressed state of the elastic pressing part 11 is released after the needle rod 22 is fully inserted, the hook 8 is inserted into the needle hole 24 of the needle rod through the intermediate hole 14, so the needle rod 22 becomes engaged at the upper abdominal wall fixer 1.

When the needle rod is disengaged from the upper abdominal wall fixer 1, it is disengaged through the above described ways.

The first embodiment of the present invention may further comprise a plate shaped fixing part 5 which is formed of a guide part 6 guiding the hook connection part 10 and a hook guide part 7 guiding the hook 8.

The guide part 6 and the hook guide part 7 may be implemented by forming a guide groove at a plate member or by attaching a guide tube at a plate member.

When the needle rod 22 is fixed at the upper and lower abdominal wall fixers, respectively, the elastic part 21 is compressed, so the length of the lower side of the body part 3 of the upper abdominal wall fixer shrinks, whereby the lower circular plate 2 and the abdominal wall 100 come to close contact with each other with the aid of the elastic force of the elastic part (not shown).

Figure 4:
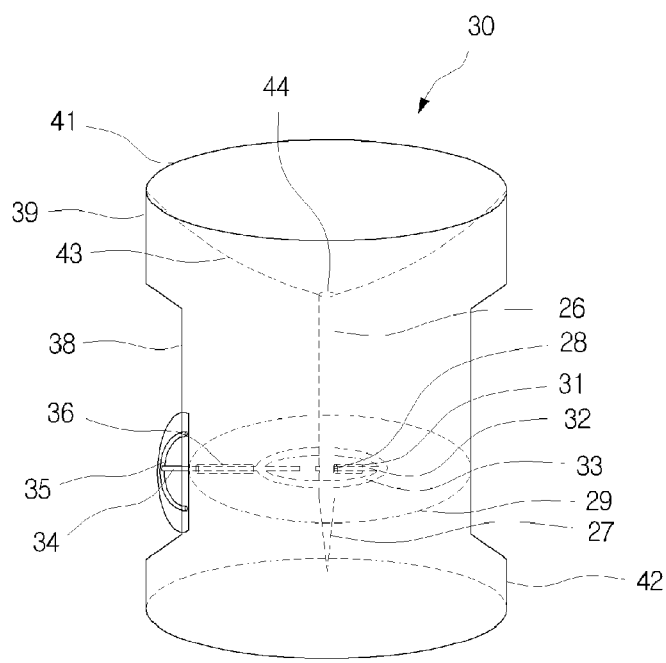
FIG. 4 is a view illustrating a construction of a lower abdominal fixer of a retraction system for a laparoscopic surgery according to a first embodiment of the present invention.

FIG. 4 is a view illustrating a construction of the lower abdominal wall fixer 30 according to a first embodiment of the present invention.

The lower abdominal wall fixer 30 according to a first embodiment of the present invention has feature in that the cylindrical rim parts 39 and 42 are formed at the upper and lower sides, and it comprises a central body part 38 which is formed a bit inwards rather than the cylindrical rim parts 39 and 42, which can be caught by a laparoscopic surgery tool (not shown).

The upper side of the lower abdominal wall fixer 30 has a lower guide hole 44 allowing a needle rod to pass by at the center portion, and a hopper shaped upper plate 43 which is inclined downwards from the upper side of the upper rim part to the guide hole 44.

A lower needle rod guide tube 26 is formed at the lower side of the upper plate 43.

A needle shaped finishing part 27 is provided at a lower end of the lower needle rod guide tube 26 for the purpose of limiting an entering of the needle at the end of the needle rod 22.

At the outer side of the central body part 38 is disposed a lower elastic pressing part 35 which has the same construction as when a needle rod is engaged in the upper abdominal wall fixer 1, and in the interior of the central body part 38 are provided at a lower side of the hook connection part 34 and the lower circular hook part 33 which operate in sync with the lower elastic pressing part 35.

At both sides of an intermediate portion of the lower needle rod guide tube 26 is formed a lower intermediate hole 28 through which a lower hook 33 fixing the needle rod 22 comes in and goes out.

In details, the lower hook is installed in a circular hooking part near the intermediate hole for the purpose of limiting the coming-in and going-out in the intermediate hole of the needle rod guide tube, by which the needle rod can be fixed or can pass by under control.

The lower hook 33 is provided at an inner portion of one side of the lower circular hook part 33, and the lower hook connection part 33 is connected to an outer portion of one side of the circular hook part 33.

The lower abdominal wall fixer 30 according to a first embodiment of the present invention further comprises a lower plate shaped fixer 29 which is formed of a guide part 36 guiding the hook connection part 33 and a hook guider part 31 guiding the hook 33.

The guide part 36 and the hook guide part 31 may be implemented by forming a guide groove at the plate member or by attaching a guide tube at the plate member.

A protection membrane made of a smooth material may be further provided at the outer portions of the elastic pressing parts of the upper abdominal wall fixer and the lower abdominal wall fixer according to a first embodiment of the present invention.

In the first embodiment of the present invention, the upper and lower circular plates of the upper abdominal wall fixer of the upper and lower abdominal wall fixer, the body part upper portion, the plate shaped fixing part, the needle rod, the body part and the upper side of the lower abdominal wall fixer are made of the metallic materials such as titanium or stainless.

In addition, the upper and lower abdominal wall fixer and the needle rod according to a first embodiment of the present invention are made of a polymer containing polycarbonate and polyetheretherketon, a metal such as titanium or stainless, a composite such as a carbon-fiber-enforced PEEK, a ceramic material and a combination of them. They may be made of a semi-solid material formed of a thermoplastic elastic polymer such as polyurethane, a polyisoprene elastic polymer, middle-to-high hardness silicon elastic polymer latex and/or a combination of them.

In the first embodiment of the present invention, the body part lower portion of the upper abdominal wall fixer and the protection membrane of the elastic pressing part may be formed of a material such as a silicon elastic polymer with a flexibility, latex, a biologically adaptive PVC, etc.

The body part lower portion of the upper abdominal wall fixer and the elastic pressing part protection membrane according to a first embodiment of the present invention may be made of dacron or PET, polyester elastomer, ePTFE, polyurethane, PVC, polycarbonate, a polymer containing polyetheretherketon, fluorocarbon, polyacetal, polyolefin, silicon elastic polymer, latex and/or a combination of them.

The procedure for fixing a lower abdominal wall fixer at an abdominal wall is as follows.

The sharp needle 23 of the lower end of the needle rod engaged in the upper abdominal wall fixer is inserted into the abdominal cavity through the abdominal wall 100, and as shown in FIG. 4, the needle rod 22 is inserted into the lower needle rod guide tube 26 through the lower guide hole 44 formed at the center of the lower abdominal wall fixer.

At this time, the lower hook 33 is forced to part from the lower intermediate hole 28 by pressing the protection membrane of the lower elastic pressing part 35 by using the laparoscopic tool such as a dissector (not shown). When the needle rod 22 is pushed in, the needle rod 22 can be fully inserted.

After the needle rod 22 is fully inserted up to the finishing part 27 of the lower needle rod guide tube 26, when the elastic force of the lower elastic pressing part is removed, the lower hook 33 is inserted into the needle hole 25 of the needle rod 22 through the lower intermediate hole 28, so the needle rod 22 can be fixedly engaged to the lower abdominal wall fixer 30, and the upper and lower abdominal wall fixers come to be fixed at the abdominal wall with the abdominal wall 100 being between them.

The detachment can be performed in the same ways as the above described ways when detaching the needle rod 22 from the lower abdominal wall fixer.

Figure 5:
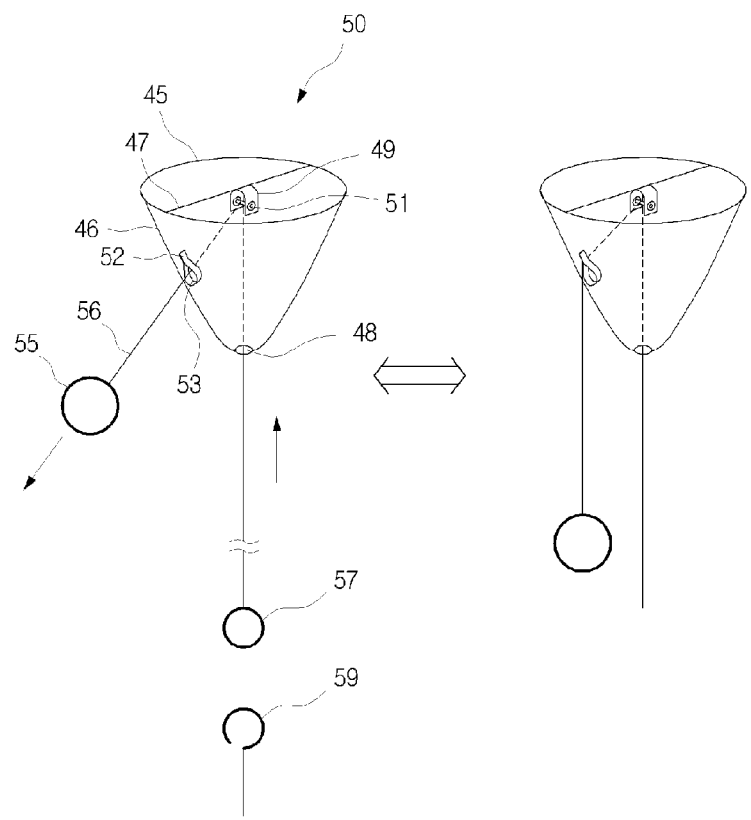
FIG. 5 is a view illustrating a construction a retraction fiber control part of a retraction system for a laparoscopic surgery according to a first embodiment of the present invention.

FIG. 5 is a view illustrating a construction of a retraction fiber control part 50 of the retraction system according to a first embodiment of the present invention.

The retraction fiber control part 50 comprises a circular cone shaped retraction fiber control part body 46 with its upper side being wide and its lower side being narrow, and a retraction hole 48 formed at the apex of the lower side of the retraction fiber control part body 46, through which retraction hole 48 a retraction fiber comes in and goes out.

At the top of the retraction fiber control part body 46 is formed a pulley engaging support wire 47 with a certain diameter at its upper circumference, so a pulley body 49 with a pulley 51 is installed at the support wire 47.

The top of the retraction fiber control part body 46 is covered with a support plate, and the pulley body 49 is installed at the top of the same, and a space through which the retraction fiber 56 comes in and goes out is formed at its lower side.

At a side surface of the retraction fiber control part body 46 is formed a retraction fiber side hole 53 through which a retraction fiber retracted by the pulley comes in and goes out along the side surface of the retraction fiber control part body 46. At an outer portion of the retraction fiber side hole 53 is engaged a retraction fiber fixing part 52 with an insertion part retracting and fixing a retraction fiber.

As shown in FIG. 5, the retraction fiber fixing part 52 is longitudinally formed at an acute angle with its upper side being gradually narrowed and its lower side being formed in a circular shape.

The circular member 55 connected to a retraction fiber may be retracted by pulling it through the retraction fiber side hole 53, and the retraction fiber may be fixed by inserting a retraction fiber into the insertion part formed at an acute angle portion of the upper side of the retraction fiber fixing part 52.

The retraction fiber 56 retracted through the retraction fiber hole 48 is guided by the pulley 51 and is retracted through the retraction fiber side hole 53.

During the operations, the circular member 55 may be retracted or fixed using a laparoscopic tool.

The retraction fiber connecting down through the retraction fiber hole 48 may be directly connected with a retraction part which is retracted or a retraction fiber may be connected at an intermediate portion by forming a circular ring 57 at an intermediate portion.

The circular ring and the circular member may be installed at either the retraction controller or the retraction part or they may be installed switched with each other.

In an embodiment of the present invention, the installation of the connection part near the retraction part make easier the connection work.

A retraction fiber may be connected in a pair or with a bolt and a nut instead of the above mentioned circular ring and the circular member and a retraction part.

According to the abdominal wall fixer according to an embodiment of the present invention, any damages don't occur due to the use of the retraction system in such a way that it can be attached at the abdominal wall with a thin needle rod.

The retraction fiber control part body, the pulley, the retraction fiber fixing part, the support wire or the support plate may be made of a polymer containing polycarbonate and polyetheretherketon, a metal such as titanium or stainless, a composite such as a carbon-fiber-enforced PEEK, a ceramic material and a combination of them. In addition, they may be made of a flexible semi-solid material formed of a thermoplastic elastic polymer such as polyurethane, a polyisoprene elastic polymer, middle-to-high hardness silicon elastic polymer latex and/or a combination of them.

In the embodiment of the present invention, the retraction fiber control part body, the pulley, the retraction fiber fixing part, the support wire and the support plate may be made of a composite such as a carbon and fiber-reinforced PEEK or a ceramic material.

In the embodiment of the present invention, the retraction fiber fixing part is made of a polymer containing polycarbonate and polyetheretherketon.

Figure 6:
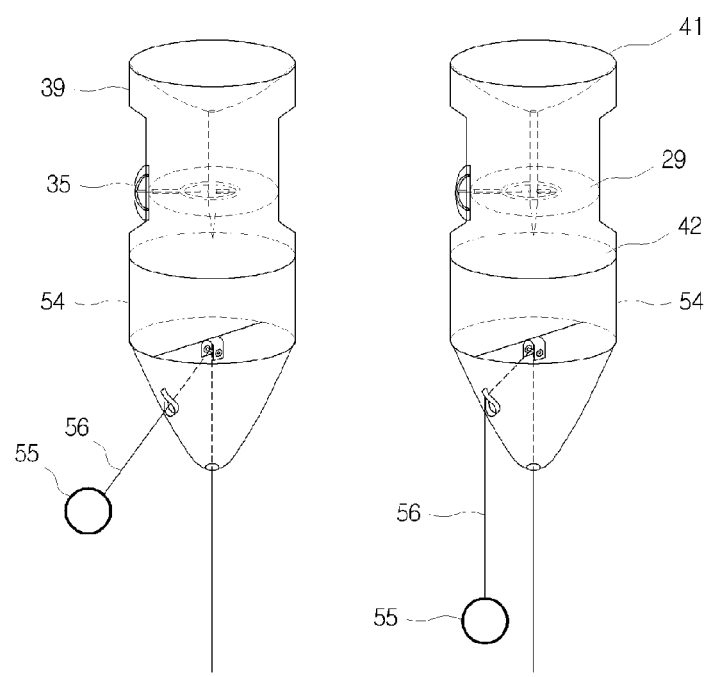
FIG. 6 is a view illustrating a construction that a lower abdominal wall fixer and a retraction fiber control part are engaged according to a first embodiment of the present invention.

FIG. 6 is a view illustrating a construction that a lower abdominal fixer and a retraction fiber control part 50 are engaged in a retraction system according to a first embodiment of the present invention.

The retraction fiber 50 of the control part is connected with a lower abdominal wall fixer and a connection membrane 54, and the connection membrane 54 is fixedly attached to the circumference of the top of the retraction fiber control part 50 and the lower rim part 42 of the lower abdominal wall fixer with the aid of a bonding or a thermal welding.

The connection membrane 54 may be made of dacron or PET, polyester elastomer, ePTFE, polyurethane, PVC, polycarbonate, a polymer containing polyetheretherketon, fluorocarbon, polyacetal, polyolefin, silicon elastic polymer, latex and/or a combination of them.

In the embodiments of the present invention, the lower abdominal wall fixer connection membrane 54 is made of a silicon elastic polymer with flexibility, latex and a biologically adaptive PVC.

Figure 7:
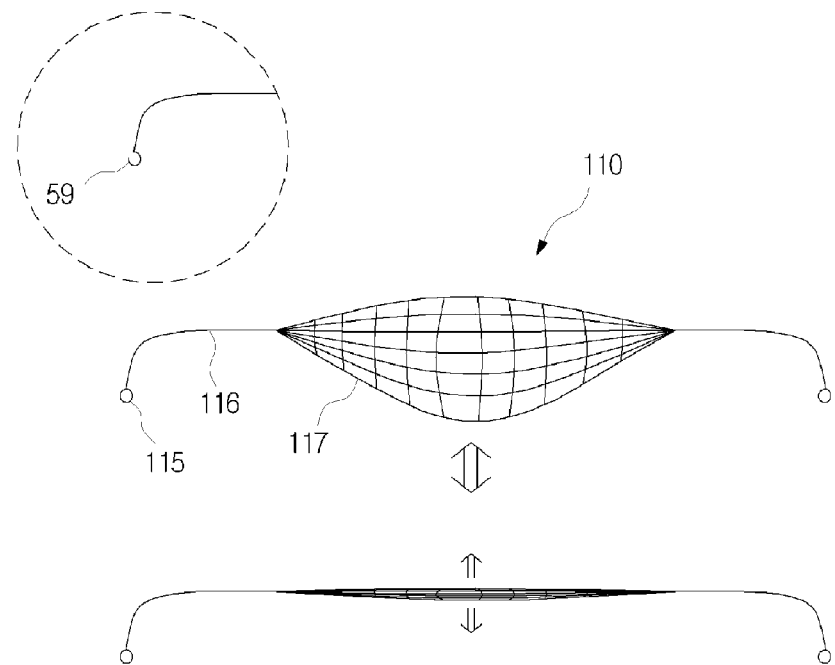
FIG. 7 is a view illustrating a construction of a tissue retractor of a retraction system for a laparoscopic surgery according to a second embodiment of the present invention.

FIG. 7 is a view illustrating a construction of a tissue retractor of a retraction system for a laparoscopic surgery according to a second embodiment of the present invention.

The tissue retractor 110 comprises a net-shaped net retraction net 117 formed of a smooth fiber or cotton cloth, a retraction fiber 56 connected to both ends of the net retraction net, and a circular member 115 connected to the retraction fiber.

The net retraction net 117 of the tissue retractor 110 is made of a filament, a short staple fiber, a spun yarn, a blended yarn, a single yarn, a twisted yarn, a plaited thread, a weaving yarn, a knitting yarn, a carded yarn, a combed yarn, a woolen yarn, a worsted yarn, a left twisted yarn, a right twisted yarn, a high twist yarn, a soft twist yarn, a multi-lobal yarn, a metallic yarn, a lurex yarn, an A/A yarn, a tow yarn, a core piled yarn, a covering yarn, a decoration yarn, a grandrelle yarn, a stub yarn, a loop yarn, a knop yarn, a knot yarn, a spiral yarn and a combination of them.

The tissue retractor 110 may spread upwards or downwards with a laparoscopic tool (not shown) as it covers an organ or a tissue (such as liver or uterus) to be retracted.

The retraction fiber 56 connected to both ends of the net retraction net 117 in the tissue retractor 110 may be directly connected to the above mentioned retraction fiber control part 50.

In the tissue retractor 110, it may be connected by inserting the circular member 115, which is connected to the retraction fiber 56 connected to both ends of the net retraction net 117, into the circular ring 57 of the retraction fiber control part 50.

It may be connected in such a way that the circular ring 59 (the portion indicated by a dotted line in FIG. 7) is engaged instead of the circular member 115 and is inserted into the circular member of the controller 50.

The circular member or the circular ring which is connected to a retraction fiber may be made of a polymer containing polycarbonate and polyetheretherketon, a metal such as titanium or stainless, a composite such as a carbon-fiber-enforced PEEK, a ceramic material and a combination of them. They may be made of a semi-solid material formed of a thermoplastic elastic polymer such as polyurethane, a polyisoprene elastic polymer, middle-to-high hardness silicon elastic polymer latex and/or a combination of them.

The circular member and the ring connected to a retraction fiber according to an embodiment of the present invention may be made of a composite such as a carbon-fiber-enforced PEEK or a ceramic material.

Figure 8:
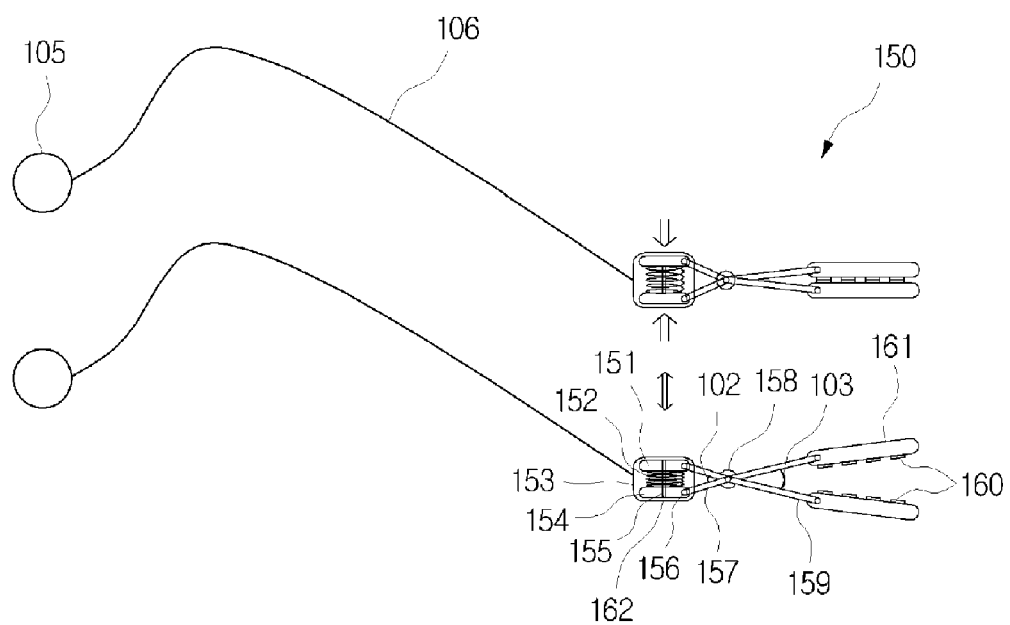
FIG. 8 is a view illustrating a grasper of a retraction system for a laparoscopic surgery according to a third embodiment of the present invention.

FIG. 8 is a view illustrating a construction of a grabber retractor of a retraction system for a laparoscopic surgery according to a third embodiment of the present invention.

The grabber retractor is a retraction system which helps grab an organ or a tissue (gallbladder or stomach, intestine or intestine membrane) to be retracted, with the aid of a laparoscopic tool.

The grabber retractor 150 comprises a body part waterproof membrane 153 covered with a grabber body part starting an opening operation with a laparoscopic tool and a waterproof protection membrane waterproofing an outer side of the grabber body part, a head part 161 with a protrusion 160 helping grab a tissue or an organ, a head part rod 159 connecting the head part, a maintaining spring 103 connected between the head part rods for temporarily maintaining an opened state of the head part, a body part rod 157 connected to the upper and lower plates of the body part and transferring the operation of the grabber body part to the head part about a pivot 158, and a maintaining spring 102 temporarily maintaining an opened state of the grabber body part.

The grabber body part comprises a grabber upper plate 151, a grabber lower plate 154, a plate connection part 155 movably connecting the grabber upper plate and lower plate, a grabber through needle 162 passing though the interior of the grabber upper plate and lower plate after it passes through the interior of the plate connection part 155, and a coil spring-shaped elastic part 152 which is positioned at the grabber upper plate and lower plate and maintains the closed state of the grabber head part 160 by elastically widening the grabber upper plate and the grabber lower plate when in usual time.

The grabber body part is connected by the retraction fiber 106 connected with the circular member 102, and the retraction fiber 106 may be directly connected with the retraction fiber control part 50 attached at the above mentioned abdominal fixer.

It may be connected by inserting the circular member 105 connected to the retraction fiber 106 into the circular ring 57 of the retraction fiber control part 50.

When the use of the grabber retractor 150 is stopped or it is in temporal standby, it is retracted to one side by the retraction fiber control part 50 and returns to a work place when in use.

When the body part protection membrane 153 is pressed holding the laparoscopic tool (not shown), the coil spring shaped elastic part 152 shrinks in the interior of the grabber body part protection membrane, and the grabber head part 160 operating in sync with the same opens.

When the pressing motion is stopped, the grabber head part 160 is closed by the recovering force of the elastic part 152.

When the grabber body part protection membrane 153 is pressed upwards and downwards with the laparoscopic tool (not shown), the grabber upper plate 151 and the grabber lower plate 154 are pressed, and the coil spring shaped or wave spring shaped elastic part 152 in the interior is compressed, and the grabber through needle 63 passes through the interiors of the grabber upper plate and lower plate and comes into the groove formed at the ends of the upper and lower plates and becomes flat.

The grabber head part 161 opens by the body part rod 157 and the head part rod 159 which operate in sync with the same, and the opened grabber head part 161 grabs an organ or a tissue (gallbladder, stomach, intestine or intestine membrane) which is to be retracted.

When it is necessary to separate the organ or the tissue from the grabber retractor 150, the same procedures are performed.

In the embodiments of the present invention, there is provided a retraction system for a surgical operation which makes it possible to temporarily support a surgical operation tool such as a grabber, etc. which is in standby for the actual use during the laparoscopic surgery, so it is possible to reduce the number of the trocars, reducing the scars after surgical operations.

The embodiment of the present invention has features in that the grabber body part protection membrane 154 is made of a silicon elastic polymer with a flexibility, latex, a biologically adaptive PVC, etc.

The grabber head part, the grabber body part, the grabber upper plate and lower plate and the through needle are made of a polymer containing polycarbonate and polyetheretherketon, a metal such as titanium or stainless, a composite such as a carbon-fiber-enforced PEEK, a ceramic material and a combination of them.

In addition, they may be made of a flexible semi-solid material formed of a thermoplastic elastic polymer such as polyurethane, a polyisoprene elastic polymer, middle-to-high hardness silicon elastic polymer latex and/or a combination of them.

According to another embodiment of the present invention, The grabber head part, the grabber body part, the grabber upper plate and lower plate and the through needle are made of a material such as a polymer containing polycarbonate and polyetheretherketon.

The grabber body part protection membrane 153 is made of dacron or PET, polyester elastomer, ePTFE, polyurethane, PVC, polycarbonate, a polymer containing polyetheretherketon, fluorocarbon, polyacetal, polyolefin, silicon elastic polymer, latex and/or a combination of them.

Figure 9:
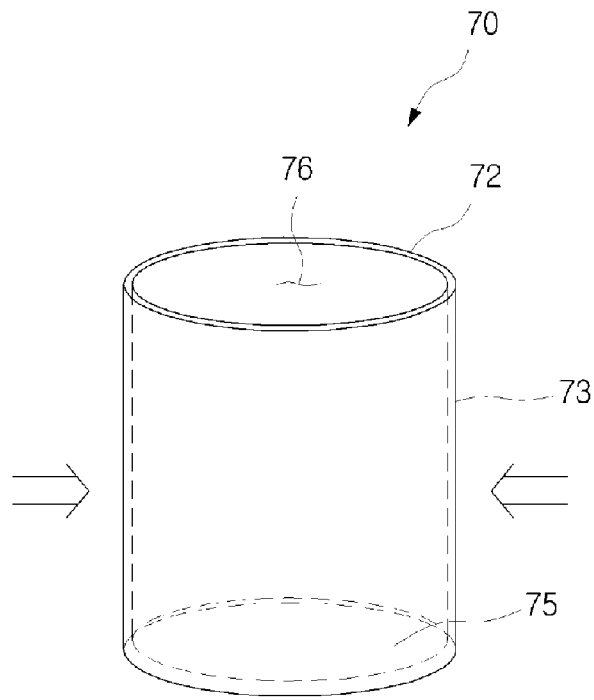
FIG. 9 is a view illustrating a lower abdominal wall fixer of a retraction system for a laparoscopic surgery according to a fourth embodiment of the present invention.

FIG. 9 is a view illustrating a construction of an abdominal wall fixer 70 which can be attached to a lower side of the retraction system for a laparoscopic surgery according to a fourth embodiment of the present invention.

The attachable abdominal wall fixer 70 has features in that the upper part 76 is open, and the lower part 75 is formed of a sealed cylindrical body.

The upper rim part 72 of the cylindrical body is made of a flexible elastic part for the purpose of always maintaining a circular shape. The intermediate part 73 of the cylindrical body is made of an elastic material which can be easily grabbed with a laparoscopic tool (not shown) and can easily recover its shape when the laparoscopic tool is released.

The attachable abdominal wall fixer 70 has features in that in a state that the intermediate part 73 of the cylindrical body is pressed and held and attached to the abdominal wall with a laparoscopic tool, when the laparoscopic tool is released, the portion pressed by the laparoscopic tool recovers elastically, and the pressure of the interior becomes lower than the outside for thereby generating a negative pressure.

The attachable abdominal wall fixer is fixedly attached to the abdominal wall with the aid of the negative pressure, and when both cylindrical sides are held with the laparoscopic tool, the negative pressure is removed, so it can be removed from the abdominal wall.

The attachable abdominal wall fixer 70 is made of dacron of an elastic material or PET, polyester elastomer, ePTFE, polyurethane, PVC, polycarbonate, a polymer containing polyetheretherketon, fluorocarbon, polyacetal, polyolefin, silicon elastic polymer, latex and/or a combination of them.

In the embodiments of the present invention, the attachable abdominal wall fixer is made of a material containing silicon elastic polymer and latex.

The attachable abdominal wall fixer according to an embodiment of the present invention has features in that it can be easily attached or detached with the aid of the laparoscopic tool, and since it is directly attached to an abdominal wall without leaving any damages in the abdominal wall, the operation time reduces, and any damages due to the use of the retraction system don't happen.

Figure 10:
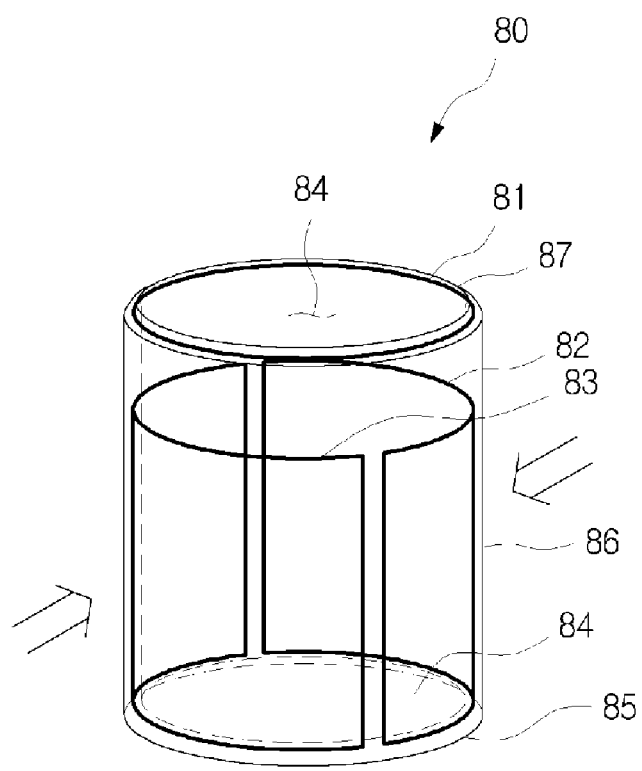
FIG. 10 is a view illustrating a construction that an elastic member is secured to an inner side of a lower abdominal wall fixer according to a fourth embodiment of the present invention.

FIG. 10 is a view illustrating a construction that an elastic part is engaged in the interior of the attachable abdominal fixer of the retraction system for a laparoscopic surgery according to a fourth embodiment of the present invention.

The elastic part attachable abdominal wall fixer 80 is formed of a cylindrical body the upper part 84 of which is open, and the lower part 84 is sealed.

The upper rim 87 of the cylindrical body has an elastic ring 61 made of an elastic material always maintaining a circular shape, and semicircular plate-shaped elastic parts 82 and 83 are symmetrically provided in the interior of the cylindrical body for thereby maintaining a cylindrical shape all the time.

When the laparoscopic tool is released in a state that it is attached to an abdominal wall, holding the intermediate portion of the cylindrical body of the elastic part attachable abdominal wall fixer 80, the portion pressed by the laparoscopic tool is elastically recovered, so the pressure of the interior becomes lower than the pressure of the outside, whereby a negative pressure generates at the attached surface of the elastic part attachable abdominal wall fixer 80.

The elastic part attachable abdominal wall fixer is fixedly attached to the abdominal wall with the aid of the negative pressure, and the negative pressure is removed when holding both sides of the cylindrical shape with the laparoscopic tool, so it can be easily separated from the abdominal wall.

The cylindrical body of the attachable abdominal wall fixer is made of dacron or PET, polyester elastomer, ePTFE, polyurethane, PVC, polycarbonate, a polymer containing polyetheretherketon, fluorocarbon, polyacetal, polyolefin, silicon elastic polymer, latex and/or a combination of them.

In the embodiment of the present invention, the cylindrical body of the elastic part attachable abdominal wall fixer is made of a material containing silicon elastic polymer and latex.

The semicircular plate shaped elastic part and the elastic ring of the elastic part attachable abdominal wall fixer is made of a polymer containing polycarbonate and polyetheretherketon, a metal such as titanium or stainless, a composite such as a carbon-fiber-enforced PEEK, a ceramic material and a combination of them. In addition, they may be made of a semi-solid material formed of a thermoplastic elastic polymer such as polyurethane, a polyisoprene elastic polymer, middle-to-high hardness silicon elastic polymer latex and/or a combination of them.

The semicircular plate shaped elastic part and the elastic ring in the embodiment of the present invention is made of a polymer containing polycarbonate and polyetheretherketon.

Figure 11:
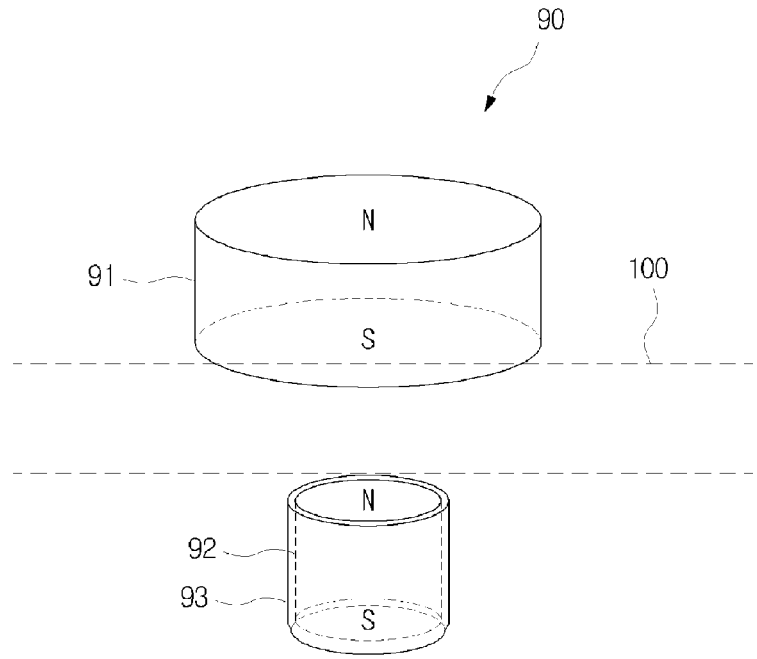
FIG. 11 is a view illustrating a construction of a magnet part abdominal wall fixer according to a fifth embodiment of the present invention.

FIG. 11 is a view illustrating a construction of a magnet part abdominal wall fixer using a magnetic force according to a fifth embodiment of the present invention.

The magnet part abdominal wall fixer 90 comprises an upper abdominal wall fixed magnet part 91 formed of a circular plate shaped magnet, a lower abdominal wall fixed magnet 92 which is arranged opposite to the magnetic force of the upper abdominal wall fixed magnet part, and a protection membrane 93 surrounding the lower abdominal wall fixed magnet.

The upper abdominal wall fixed magnet part 91 gets contacted with the abdominal wall 100, and the lower abdominal wall fixed magnet part is held with a laparoscopic tool (not shown) and gets contacted with the abdominal wall, so it can be fixed at the abdominal wall with the aid of the magnetic force of the magnet.

The retraction fiber control part 50 is engaged to the lower side of the lower abdominal wall fixed magnet part with the aid of the connection membrane 54 which was described in the descriptions of the embodiment of FIG. 6, so the objects to be retracted in the abdominal cavity can be retracted.

The membrane 93 surrounding the lower abdominal wall fixed magnet is made of dacron or PET, polyester elastomer, ePTFE, polyurethane, PVC, polycarbonate, a polymer containing polyetheretherketon, fluorocarbon, polyacetal, polyolefin, silicon elastic polymer, latex and/or a combination of them.

In the embodiment of the present invention, the protection membrane 93 surrounding the lower abdominal wall fixed magnet is made of a material such as silicon elastic polymer with a flexibility, latex, a biologically adaptive PVC, etc.

Figure 12:
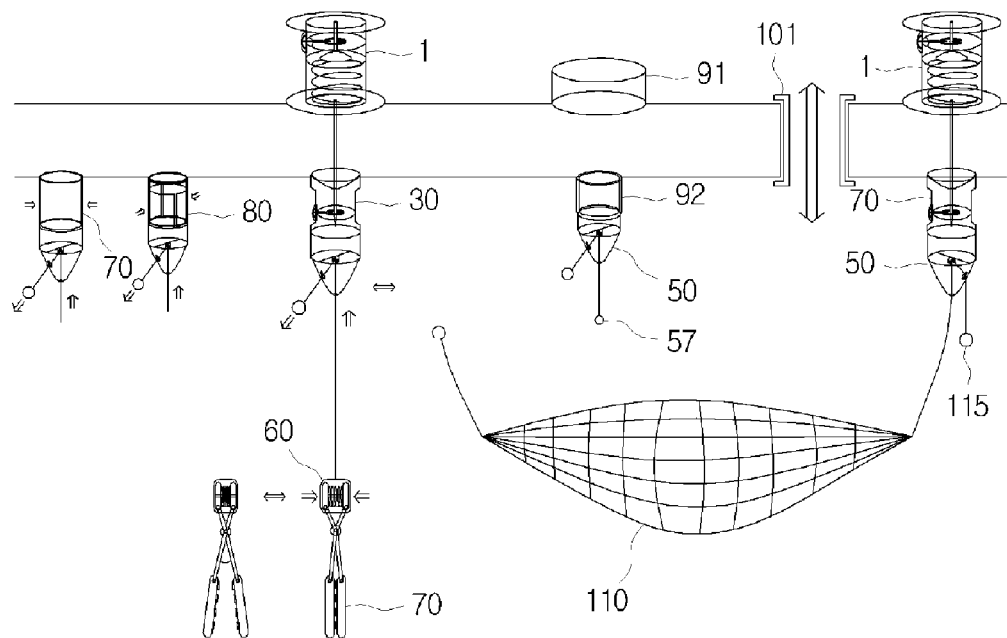
FIG. 12 is a view illustrating a construction of a retraction system for a laparoscopic surgery according to an embodiment of the present invention.

FIG. 12 is a view illustrating a construction of a retraction system according to an embodiment of the present invention.

The retraction system according to an embodiment of the present invention is inserted through the cut window or the trocar 101 formed at the abdominal wall.

The abdominal wall fixer inserted into the abdominal cavity through the cut window or the trocar is fixed at the abdominal wall, and the net-shaped tissue retractor 110 surrounds an organ or a tissue (for example, liver or uterus) to be retracted by the laparoscopic tool (not shown), and it is retracted and fixed by the abdominal wall fixer of a necessary space.

The retraction system according to an embodiment of the present invention has features in that an intestine such as a gallbladder, small intestine (including duodenum), large intestine, rectum or stomach can be protected in the course of laparoscopic surgery, and it is possible to prevent the intestines from coming down into the surgical operation region.

The operation procedures and the operation view ways are not interfered with other organs and operation tools during the laparoscopic surgery, thus reducing operation time.

When the use of the grabber retractor 150 is temporarily stopped or it is in temporal standby, the portion where the abdominal wall fixer is fixed in the abdominal cavity can be separated from the abdominal all and is retracted to one side, and then it can be moved toward a work place only when in use, so any collisions between the tools can be prevented, and an operation space and operation view ways can be obtained.

Since there is provided an abdominal wall fixer which can have the tissue retractor and the operation tools, which are ready for actual uses, temporarily supported at the abdominal wall without using a trocar for a surgical operation, it is possible to minimize the number of the operation tools when in use in the cut window or the passages in the abdominal cavity such as a trocar system positioned in the cut window in terms of a scar retraction function, so collisions between the tools when retracting a tissue can be prevented, thus reducing the operation time.

The retraction system according to an embodiment of the present invention is directed to a retraction system for a surgical operation which has a desired retraction function of handling a laparoscopic surgery in an abdominal cavity, so the number of trocars can be reduced, and the scars after the surgical operation can be minimized.

When the operation is finished or it is necessary to remove the retraction system, the parts inserted in the abdominal cavity of the retraction system are removed with the laparoscopic tools through the cut window or the trocars.

INDUSTRIAL APPLICABILITY

The present invention is directed to a retraction system which is used to retract a tissue or an internal organ during surgical operations in terms of a laparoscopic surgery, a thoracoscopic surgery, a robot-assisted surgery, etc.

The invention claimed is:
1. A refraction system for a laparoscopic surgery, comprising:
 a refraction part for holding an object or a tissue which will be refracted;

a refraction fiber control part for refracting the retraction part with a retraction fiber to a retraction place and fixing the refraction part; and an abdominal wall fixer which is coupled with the refraction fiber control part and is configured to be fixed at an abdominal wall, and the refraction fiber control part comprising:

a retraction fiber controller body which has a refraction hole formed at a lower side for a retraction fiber connected with the retraction part to pass through the retraction hole; and a retraction fiber fixer which is provided at an outer side of the retraction fiber controller body and retracts the retraction fiber and fixes the retraction fiber, wherein the abdominal wall fixer comprises:

an upper abdominal wall fixer which is configured to be secured to an outer side of the abdominal wall; and a lower abdominal wall fixer which is configured to be secured in the interior of the abdominal wall and the upper abdominal wall fixer and the lower abdominal wall fixer are configured to be secured at the inner and outer sides of the abdominal wall with the aid of the lower abdominal wall fixer and a needle rod formed of an en raging needle hole, wherein the lower abdominal wall fixer comprises:

a cylindrical body with a concave upper plate;

a needle rod guide tube which is connected with the upper plate and guides the downward insertion of the needle rod;

a needle shaped finishing part which is formed at a lower end portion of an end of the needle rod when the end is inserted into the needle rod guide tube;

a hook which is installed near the intermediate hole for limiting the coming-in and going-out through the intermediate hole of the needle rod guide tube and controlling for the end of the needle rod can be fixed or can pass by; and an elastic pressing part which is engaged at an outer portion of the cylindrical body and controls the coming-in and going-out of the hook in sync with the hook.

2. The system of claim 1, wherein the retraction fiber fixer is formed at an acute angle relative to a longitudinal axis of the retraction fiber control part with an upper side being gradually narrowed and a lower side being formed in a circular shape and comprises an insertion part which helps retract the retraction fiber through a lower side of the retraction fiber fixing part and a retraction side hole formed at the retraction fiber controller body and helps fixedly insert the retraction fiber into the acute angle of the upper side of the retraction fiber fixing part.

3. The system of claim 2, wherein the retraction fiber fixer comprises a pulley part which is disposed at the top of the retraction fiber controller body and guides the retraction fiber.

4. The system of any one of claim 3, wherein the refraction system is inserted into an abdominal cavity and is separated from through a cut window provided at the abdominal wall or a trocar, and a diameter of the refraction system is 5-20 mm.

5. The system of claim 2, wherein the retraction fiber that passes through the retraction side hole comprises an end portion that includes a ring or a circular member for connecting the retraction fiber to the retraction part.

6. The system of any one of claim 5, wherein the refraction system is inserted into an abdominal cavity and is separated from through a cut window provided at the abdominal wall or a trocar, and a diameter of the refraction system is 5-20 mm.

7. The system of any one of claim 2, wherein the retraction system is configured to be inserted into an abdominal cavity and is separated from through a cut window configured to be provided at the abdominal wall or a trocar, and a diameter of the retraction system is 5-20 mm.

8. The system of claim 1, wherein the refraction part comprises a net and a tissue refractor disposed at both sides of the net and connected with the refraction fiber.

9. The system of any one of claim 8, wherein the refraction system is inserted into an abdominal cavity and is separated from through a cut window provided at the abdominal wall or a trocar, and a diameter of the refraction system is 5-20 mm.

10. The system of claim 1, wherein the abdominal wall fixer is a hollow cylindrical body with an upper side being open and a lower side being sealed, and an upper rim part of the cylindrical body is formed of a flexible elastic element retaining a circular shape and the cylindrical body is made of an elastic material for the cylindrical body to inwardly transform when a laparoscopic tool grabs and to recover to an original cylindrical shape when the laparoscopic tool is released and comprises an attachable abdominal wall fixer which is attached to an inner side of the abdominal wall.

11. The system of claim 10, wherein the upper rim part comprises a circular elastic ring and symmetrical semicircular plate shaped elastic parts are arranged in a longitudinal direction in the interior of the cylindrical body.

12. The system of any one of claim 11, wherein the refraction system is inserted into an abdominal cavity and is separated from through a cut window provided at the abdominal wall or a trocar, and a diameter of the refraction system is 5-20 mm.

13. The system of any one of claim 10, wherein the refraction system is inserted into an abdominal cavity and is separated from through a cut window provided at the abdominal wall or a trocar, and a diameter of the refraction system is 5-20 mm.

14. The system of claim 1, wherein the upper abdominal wall fixer comprises:

a cylindrical body formed of upper and lower circular plates;

a needle rod guide tube which is connected with the upper circular plate for guiding the insertion of the needle rod toward a lower side;

a spring guide plate formed at the lower side of the needle rod guide tube;

a spring which is disposed between the spring guide plate and the lower circular plate;

a hook which is installed near an intermediate hole for limiting the coming-in and going-out through the intermediate hole of the needle rod guide tube for thereby either fixing or passing the needle rod; and an elastic pressing part which is secured to an outer side of the cylindrical body and controls the hook.

15. The system of claim 14, wherein the elastic pressing part is formed in a bow shape bent outwardly, one end of which operates in sync with the hook and the other end of which slides on the lower abdominal wall fixer or the upper abdominal wall fixer body, and when a pressing force is applied to an outer side of the hook, the hook is disengaged from the intermediate hole, so the needle rod can be inserted, and when the pressing force is removed and the needle rod is fully inserted, the hook becomes inserted into the intermediate hole and a needle hole thanks to the elastic force from the bow shape, so the needle rod can be fixed.

16. The system of any one of claim 14, wherein the refraction system is inserted into an abdominal cavity and is separated from through a cut window provided at the abdominal wall or a trocar, and a diameter of the refraction system is 5-20 mm.

17. The system of any one of claim 1, wherein the refraction system is inserted into an abdominal cavity and is separated from through a cut window provided at the abdominal wall or a trocar, and a diameter of the refraction system is 5-20 mm.

18. The system of claim 1, wherein the refraction part comprises:
   a grabber refractor, comprising:
   a head part with a protrusion that configured to grab an organ or a tissue; and
   a grabber body part controlling an opening and closing operation of the head part, and when a pressing force is applied to the grabber body part, the head part is opened, and when the pressing force is removed, the head part is closed.

19. The system of claim 18, further comprising:
   an open spring disposed between an upper plate and a lower plate of the grabber body part;
   a body part rod connected to the upper plate and the lower plate, respectively;
   a head part rod which is pivoted at the body part rod and transfers an opening and closing operation of the grabber body part to the head part; and
   a body part waterproof membrane which surrounds an outer side of the grabber body part with a waterproof protection membrane.

20. The system of claim 1, wherein the abdominal wall fixer comprises:
   a lower abdominal wall fixed magnet part which is disposed in an interior of the abdominal wall and is formed of a magnet; and
   an upper abdominal wall fixed magnet part which is secured to an outer side of the abdominal wall and has a magnetism opposite to the magnetism of the lower abdominal wall fixed magnet part, and the upper and lower abdominal wall fixed magnet parts each comprise a protection membrane surrounding the fixed magnet parts.

21. The system of any one of claim 1, wherein the retraction system is inserted into an abdominal cavity and is separated from through a cut window provided at the abdominal wall or a trocar, and a diameter of the refraction system is 5-20 mm.

22. The system of any one of claim 1, wherein the retraction system is configured to be inserted into an abdominal cavity and is separated from through a cut window configured to be provided at the abdominal wall or a trocar, and a diameter of the retraction system is 5-20 mm.

23. The system of claim 1, wherein the elastic pressing part is formed in a bow shape bent outwardly, one end of which operates in sync with the hook and the other end of which slides on the lower abdominal wall fixer or the upper abdominal wall fixer body, and when a pressing force is applied to an outer side of the hook, the hook is disengaged from the intermediate hole, so the needle rod can be inserted, and when the pressing force is removed and the needle rod is fully inserted, the hook becomes inserted into the intermediate hole and a needle hole thanks to the elastic force from the bow shape, so the needle rod can be fixed.

\* \* \* \* \*